(12) United States Patent
Weber et al.

(10) Patent No.: US 11,627,871 B2
(45) Date of Patent: Apr. 18, 2023

(54) MEDICAL ENDOSCOPIC INSTRUMENT

(71) Applicant: Richard Wolf GmbH, Knittlingen (DE)

(72) Inventors: Bernd Claus Weber, Karlsruhe (DE); René Handte, Enz (DE); Alessandro Impellizzeri, Pforzheim (DE); Martin Dolt, Knittlingen (DE)

(73) Assignee: RICHARD WOLF GMBH, Knittlingen (DE)

( * ) Notice: Subject to any disclaimer, the term of this patent is extended or adjusted under 35 U.S.C. 154(b) by 369 days.

(21) Appl. No.: 16/969,677

(22) PCT Filed: Feb. 12, 2019

(86) PCT No.: PCT/DE2019/200012
§ 371 (c)(1),
(2) Date: Aug. 13, 2020

(87) PCT Pub. No.: WO2019/158168
PCT Pub. Date: Aug. 22, 2019

(65) Prior Publication Data
US 2021/0007591 A1    Jan. 14, 2021

(30) Foreign Application Priority Data
Feb. 14, 2018 (DE) ..................... 10 2018 202 243.7

(51) Int. Cl.
*A61B 1/00* (2006.01)
*A61B 1/06* (2006.01)
(Continued)

(52) U.S. Cl.
CPC ........ *A61B 1/0684* (2013.01); *A61B 1/00174* (2013.01); *A61B 1/043* (2013.01); *A61B 1/05* (2013.01); *A61B 1/0646* (2013.01)

(58) Field of Classification Search
CPC ... A61B 1/0684; A61B 1/00174; A61B 1/043; A61B 1/05; A61B 1/0646; A61B 1/0676;
(Continued)

(56) References Cited

U.S. PATENT DOCUMENTS

| 8,620,410 B2 | 12/2013 | Frangioni |
| 2010/0321772 A1 | 12/2010 | Reimer et al. |

(Continued)

FOREIGN PATENT DOCUMENTS

| DE | 102005015374 A1 | 10/2006 |
| EP | 1745736 A1 | 1/2007 |

(Continued)

*Primary Examiner* — Timothy J Neal
*Assistant Examiner* — Sung Ham
(74) *Attorney, Agent, or Firm* — McGlew and Tuttle, P.C.

(57) ABSTRACT

A medical-endoscopic instrument includes a distal elongate insertion section (1), for the minimal-invasive introduction into a human or animal body, with a first LED (5), a second LED (7) and a picture sensor (9). The first LED includes a first light spectrum (19), suitable for fluorescence endoscopy. The second LED includes a second light spectrum (21), suitable for white light endoscopy. A light filter (23), arranged in front of the second LED in the viewing direction (x), has a transmission spectrum (25). The second LED is configured to irradiate according to the second light spectrum on average more intensively in a first wavelength region (K) than in a second wavelength region (L). The light filter is configured to let through light, which is emitted by the second LED, according to the transmission spectrum, on average less in the second wavelength region than in the first wavelength region.

20 Claims, 5 Drawing Sheets

(51) Int. Cl.
*A61B 1/04* (2006.01)
*A61B 1/05* (2006.01)

(58) Field of Classification Search
CPC ... A61B 1/0638; A61B 1/0653; A61B 1/0661; A61B 1/00096; A61B 1/0607; G02B 23/2461; G02B 23/243
See application file for complete search history.

(56) References Cited

U.S. PATENT DOCUMENTS

| | | | |
|---|---|---|---|
| 2011/0257484 | A1 | 10/2011 | Mizuyoshi et al. |
| 2011/0270057 | A1* | 11/2011 | Pascal ................ A61B 1/043 600/317 |
| 2012/0010465 | A1* | 1/2012 | Erikawa ............. A61B 1/0653 600/109 |
| 2012/0259174 | A1* | 10/2012 | Yamamoto ........... A61B 1/063 600/109 |
| 2013/0012815 | A1 | 1/2013 | Kubo et al. |
| 2013/0066165 | A1 | 3/2013 | Shemer et al. |
| 2013/0070071 | A1* | 3/2013 | Peltie ................. A61B 1/0638 348/68 |
| 2014/0288366 | A1 | 9/2014 | Ohkoba |

FOREIGN PATENT DOCUMENTS

| | | | |
|---|---|---|---|
| EP | 2599429 | A1 | 6/2013 |
| WO | 95/17845 | A1 | 7/1995 |
| WO | 2012069542 | A1 | 5/2012 |

\* cited by examiner

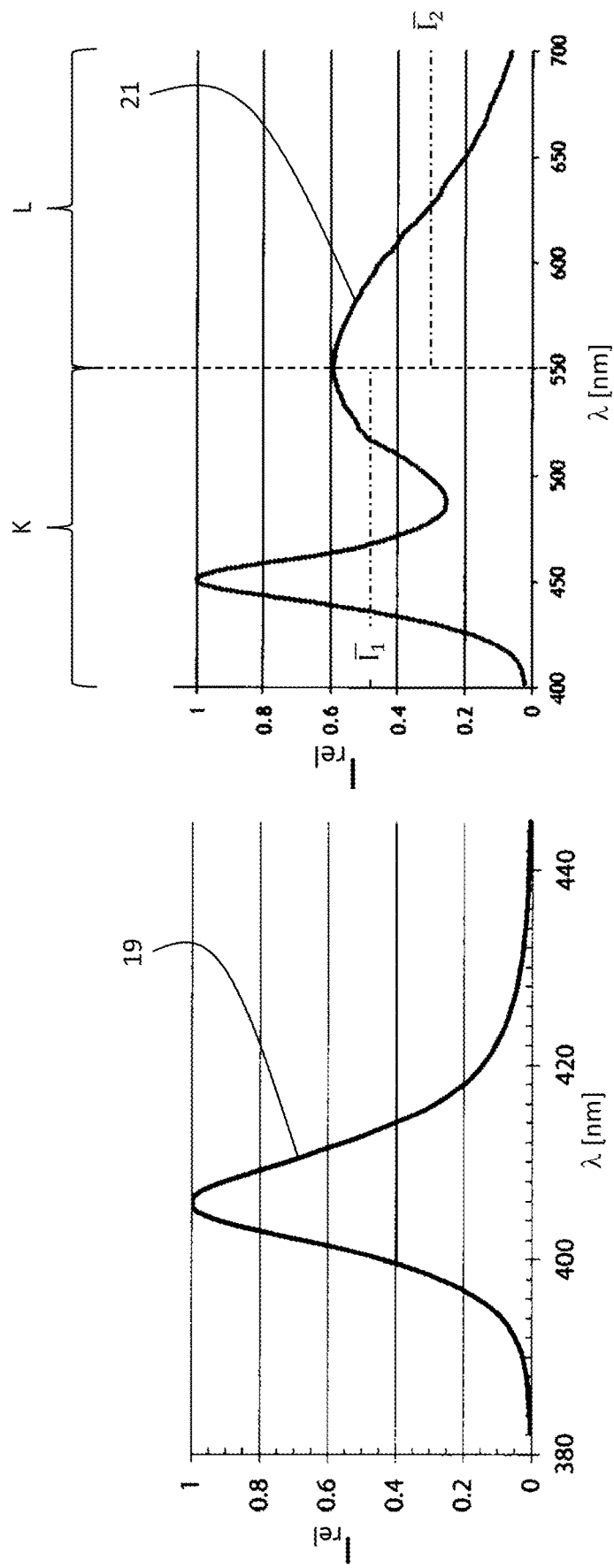

MEDICAL ENDOSCOPIC INSTRUMENT

CROSS REFERENCE TO RELATED APPLICATIONS

This application is a United States National Phase Application of International Application PCT/DE2019/200012, filed Feb. 12, 2019, and claims the benefit of priority under 35 U.S.C. § 119 of German Application 10 2018 202 243.7, filed Feb. 14, 2018, the entire contents of which are incorporated herein by reference.

TECHNICAL FIELD

The present disclosure relates to a medical-endoscopic instrument with a distal elongate insertion section for the minimal-invasive insertion into a human or animal body.

TECHNICAL BACKGROUND

It is known to use endoscopes, in order to make video recordings of the inside of a human or animal body for the purpose of a medical diagnosis and/or therapy. Herein, it is common to illuminate the inside of the body with a light source and to carry out a picture recording via a CCD sensor. Since the spectral sensitivity of a CCD sensor differs from that of a human eye, usually in the state of the art a corrective filter is placed in the picture path in front of the CCD sensor, in order to produce a natural colour impression of the recorded picture. CCD sensors are usually more sensitive that the eye, particularly in the red and infrared wavelength region, so that the applied corrective filters damp to a particularly high extent in this wavelength region. Herein however, what is disadvantageous is the fact that on account of the corrective filter, significant shares of the light power which are coupled into the inside of the body and converted into the heat there cannot be used for the picture recording of the CCD sensor.

For an improved utilisation or saving of the coupled-in light power, WO 95/17845 suggests placing a dichroic corrective filter not in the picture path of the CCD sensor, but arranging it in front of an external light source or in a fibre-optic system of the endoscope. Hence light which the CCD sensor is not to absorb is not coupled into the body in the first place. Herewith, the tissue is protected from the coupling-in of unnecessary heat and light power.

The endoscopic video system which is known from WO 95/17845 however is not suitable for the selective use in white light endoscopy and fluorescence endoscopy. In contrast to white light endoscopy, concerning fluorescence endoscopy which is used for example for the detection and localisation of pre-malignant and early malignant tissue, it is not a question of a display of the tissue in true colour, but of a fluorescence excitation with which pathological tissue can be differentiated from healthy tissue. Herein, the pathologic tissue which is excited by way of the light radiation can itself fluoresce or specifically fluoresce a bacterial build-up indicating pathological tissue and hence can be localised in a recognisable manner with respect to the surrounding health tissue. Fluorescence endoscopy can be carried out for example within the framework of a photodynamic diagnosis (PDD) and/or photodynamic therapy (PDT) by way of a photo sensibiliser or marker substance (e.g. Chlorin e6) which selectively builds up on pathological tissue.

SUMMARY

The present disclosure provides a medical-endoscopic instrument which can be selectively used for fluorescence endoscopy and for white light endoscopy and at the same time protects tissue from the coupling-in of non-used heat and light power, by way of it better utilising the coupled-in light power for the respective application purpose.

According to the present disclosure, a medical-endoscopic instrument with a distal elongate insertion section for the minimal-invasive introduction into a human or animal body is provided, wherein the insertion section comprises at least one first light-emitting diode (LED), a second LED and a picture sensor, wherein the first LED, the second LED and the picture sensor are aligned in a common viewing direction. The first LED herein comprises a first light spectrum which is suitable for fluorescence endoscopy and the second LED comprises a second light spectrum which is suitable for white light endoscopy, wherein a light filter is arranged in front of the second LED in the viewing direction. The light filter herein has a transmission spectrum, wherein the second LED is configured to irradiate according to the second light spectrum on average more intensively in a first wavelength region than in a second wavelength region and wherein the light filter is configured to let through light which is irradiated by the second LED, according to the transmission spectrum, on average less in the second wavelength region than in the first wavelength region.

What is meant by "light spectrum" here is an intensity distribution $I(\lambda)$ of the light in dependence on the wavelength $\lambda$ of the light. The average intensity in a wavelength region between a wavelength $\lambda_1$ and a wavelength $\lambda_2$ is defined here as $$\bar{I} = \int_{\lambda_1}^{\lambda_2} \frac{I(\lambda)}{\lambda_2 - \lambda_1} d\lambda.$$

What is meant by a "transmission spectrum" here is a distribution of the percentage light transparency $T(\lambda)$ in dependence on the wavelength $\lambda$ of the light. The average transmission or transparency in a wavelength region between a wavelength $\lambda_1$ and a wavelength $\lambda_2$ is here defined as $$\bar{T} = \int_{\lambda_1}^{\lambda_2} \frac{T(\lambda)}{\lambda_2 - \lambda_1} d\lambda.$$

If therefore the first wavelength region extends from a wavelength $\lambda_1$ to a wavelength $\lambda_2$ and the second wavelength region from a wavelength $\lambda_3$ to a wavelength $\lambda_4$, then $$\bar{I_1} = \int_{\lambda_1}^{\lambda_2} \frac{I_1(\lambda)}{\lambda_2 - \lambda_1} d\lambda > \bar{I_2} = \int_{\lambda_3}^{\lambda_4} \frac{I_2(\lambda)}{\lambda_4 - \lambda_3} d\lambda \text{ and}$$

$$\bar{T_1} = \int_{\lambda_1}^{\lambda_2} \frac{T_1(\lambda)}{\lambda_2 - \lambda_1} d\lambda > \bar{T_2} = \int_{\lambda_3}^{\lambda_4} \frac{T_2(\lambda)}{\lambda_4 - \lambda_3} d\lambda.$$

The average intensity $\bar{I_1}$ of the second LED in the first wavelength regions is therefore greater than the average intensity $\bar{I_2}$ of the second LED in the second wavelength region. Likewise, the average transmission or transparency $\bar{T_1}$ of the light filter in the first wavelength region is greater than the average transmission or transparency $\bar{T_2}$ of the light filter in the second wavelength region. If the functions $I(\lambda)$ and/or $T(\lambda)$ cannot be integrated locally for certain wavelengths or spectral lines in the first and/or second wavelength region, then such wavelengths or spectral lines are to be ignored on averaging. The light spectrum of the second LED and the transmission spectrum of the light filter therefore complement one another on suppressing light in the second, preferably red and infrared wavelength region. The first wavelength region can extend from a short-waved end (e.g. $\lambda_1=400$ nm) in the visible spectrum to the short-waved end (e.g. $\lambda_2=\lambda_3=550$ nm) of the second wavelength region, from which the second wavelength region extends up to a long-waved end (e.g. $\lambda_4=700$ nm) in the visible spectrum. Preferably, the first wavelength region and the second wavelength region are adjacent one another and are equally large. The first wavelength region preferably lies below the second wavelength region.

The two LEDs as light sources are arranged in the insertion section, in order to produce light "in situ" in the body, so that there is no requirement for an external light source or a fibre-optic system. Fluorescence endoscopy can be operated with the first LED and white-light endoscopy with the second LED. The picture sensor, for example a CCD sensor or CMOS sensor can be selectively used for fluorescence endoscopy and white-light endoscopy and requires no corrective filter in the form of a short-pass filter in the picture path, such reducing the light power which is available for the imaging. Fluorescence endoscopy can be carried out within the framework of PDD and/or PDT with the instrument which is disclosed here. Preferred embodiments of the instrument however can be designed predominantly for PDD, if for example the second LED has a short-waved, second light spectrum, in order to efficiently excite fluorescence. A long-waved second light spectrum with a greater penetration depth into the tissue is possibly more effective for PDT.

However, the instrument which is disclosed here has further advantages. On the one hand the LEDs laterally assume less space than a fibre optic, so that they can be placed in a very restricted construction space of the introduction section with the same viewing direction as the picture sensor, next to this. On the other hand, with the LEDS one can illuminate a greater spatial angle with an adequate brightness, in each case with less effort, for example without a scatter lens and with less optical losses, than with a fibre-optic. The light spectrum of the second LED already has a lower intensity in the second wavelength region, preferably in the red and infrared wavelength region, compared to the light spectrum of a halogen, xenon, halide or other metal vapour lamp, so that the light filter for the LED can be configured more thinly than if light of a halogen, xenon, halide or other metal vapour lamp would have to be filtered. On account of the thinner light filter, the second LED can be arranged farther "to the front" in the viewing direction on an outer surface of the insertion section, preferably its face surface, by which means a "keyhole effect" or "tunnel vision effect" is reduced and the illuminated spatial angle increased.

Here the "viewing direction" for LEDs is a main irradiation direction of the LED in the context of a Lambert beamer and for the picture sensor the main receiving/recording direction, i.e. given a planar CCD sensor or a CMOS sensor, the normal onto the sensor surface. The first LED, the second LED and the picture sensor are therefore all aligned in the same "viewing direction". The viewing direction is preferably directed distally of a face side of the insertion section, but however additionally or alternatively can also be directed laterally outwards from a lateral side of the insertion section. Concerning the face-side arrangement, "front" means in the viewing direction distally with respect to the instrument and concerning the lateral arrangement "front" means in the viewing direction laterally with respect to the instrument. Optionally therefore, the first LED, the second LED and the picture sensor can be arranged on a common wall of the insertion section. Preferably, this is a distal face side of the insertion section, wherein the viewing direction runs distally in the longitudinal direction of the insertion section. It is particularly in this embodiment that the lateral construction space for placing the first LED, the second LED and the picture sensor at the face side is very limited. Possibly, only recesses with a diameter of 1 mm to 1.5 mm per LED or picture sensor are available in the wall of the insertion section. In extreme cases, the available diameter can even be only 0.5 mm.

Optionally, the first LED can be arranged offset to the front relative to the second LED with respect to the viewing direction. Since the first LED does not use a light filter arranged in front for fluorescence endoscopy, the first LED can be arranged further to the front in the viewing direction on an outer surface of the insertion section, preferably its face side, by which means a keyhole effect is reduced and the illuminated spatial angle enlarged. The second LED is offset to the rear relative to the first LED with respect to the viewing direction due to the light filter arranged in front. Although specifically the light filter on the one hand must be thick enough, in order to be able to filter out the second wavelength region to an adequate extent, so that white light endoscopy with the picture sensor achieves a naturally as possible acting true-colour representation without an additional corrective filter in the picture path, on the other hand the light filter should be configured as thinly as possible, so that the second LED can be placed to the front as much as possible, so that the keyhole effect is reduced and the illuminated spatial angle increased.

The light filter can optionally be an absorption filter. A dichroic filter, although being advantageous in the case of an external light source with a fibre-optic system due to it heating up to a lesser extent, however it is disadvantageous for filtering in front of an LED in the insertion section compared to an absorption filter, since a dichroic filter has an angle-dependent transmission spectrum. This is less of a problem for a fibre-optic system with essentially parallel or collimated light bundles, but in the case of an LED with irradiation characteristics of a Lambert beamer leads to undesirable colour distortions. An absorption filter only has such an angular dependency of the transmission spectrum to a much lesser extent, so that undesirable colour distortions of the LED light can be neglected. Furthermore, in the case of an LED in the insertion section, the light power is significantly lower compared to an external light source, since losses in the fibre-optic system do not need to be compensated. The problem of the heating of the absorption filter and of damage to the absorption filter which is caused by way of this is therefore less pronounced in front of the second LED.

Optionally, the light filter can be an infrared blocking filter, wherein the first wavelength region lies in the visible light spectrum below 550 nm and the second wavelength region in the visible light spectrum above 550 nm. A significant share of the red and infrared light of the second LED which in any case is irradiated at a lower intensity compared to a light source other than an LED is filtered out by the light filter for white light endoscopy. The imaging on the one hand is natural and on the other hand the filtered-out long-waved light of the second LED does not unnecessarily heat the tissue. The development of heat in the light filter can be dissipated via a wall of the insertion section and/or via a coolant.

Optionally, the picture sensor in a plane which is perpendicular to the viewing direction can have essentially the same distance to the first LED as to the second LED and preferably be arranged between the first LED and the second LED. By way of this, the user can simply change between white light endoscopy and fluorescence endoscopy without the illumination angle and/or the illumination intensity or the shadowing in the picture changing too much. Although one could possibly compensate different distances by way of a different activation of the first LED and the second LED, this however would be less energy sufficient. The picture sensor is preferably arranged centrally on the face side. The first and the second LED can be arranged laterally offset thereto on the face side at a low and equal as possible lateral distance.

Optionally, the first light spectrum and the second light spectrum can be configured essentially identically or differently. The light spectra of the first and/or the second LED can each be suitable for fluorescence endoscopy as well as of white light endoscopy, independently of whether the respective light spectra are essentially identical or not. The first LED and the second LED can therefore be of the same type, i.e. be constructional identical, but this is not a necessity. It can be advantageous for the first LED to comprise a first light spectrum which is especially suitable for fluorescence endoscopy. For example, the first LED can be an LED which emits blue light for fluorescence excitation, whereas the second LED can be an LED which emits white light for white light endoscopy. The light spectrum of the first and/or the second LED above a wavelength of about 550 nm, i.e. in the second red wavelength region can reduce with an increasing wavelength, so that in contrast to a light spectrum of a halogen, xenon, halide or other metal vapour lamp, the red and infrared light shares are significantly smaller and accordingly need to be filtered out to a lesser extent for a true-colour white light endoscopy.

Optionally, the light filter can comprise a light inlet side and a light outlet side and between the light inlet side and light outlet side in the viewing direction can have a thickness and orthogonally to the viewing direction a diameter, wherein the thickness is 0.3 mm up to 80% of the diameter. The lower limit of 0.3 mm results from a minimum amount, by which the light of the second LED in the second wavelength region must be filtered, so that true-colour imaging is achieved with white light endoscopy, without a corrective filter in the picture path in front of the picture sensor. This lower limit of 0.3 mm depends predominantly on the maximal optical density of the available filter material. The upper limit of 80% results from a greatest extent to which the second LED can be arranged set back in the viewing direction due to the light filter, in order to be able to adequately illuminate a spatial angle of at least 2.24 steradians with a still tolerable keyhole effect. A ratio of diameter to thickness of the light filter of about 1.5 can be particularly advantageous. Optionally, the light filter can have a light inlet side and a light outlet side and a thickness of 0.3 mm to 1.2 mm between the light inlet side and the light outlet side in the viewing direction. For example, given a diameter of 1 mm, the light filter can be roughly 0.67 mm thick or given a diameter of 1.5 mm be about 1 mm thick.

Optionally, the distance of the light inlet side of the light filter to the light irradiation side of the second LED can be less than 30% of the thickness of the light filter in the viewing direction, ideally less than 10%. This is advantageous, in order to be able to arrange the second LED as far as possible to the front in the viewing direction, in order to be able to illuminate a large as possible spatial angle to an adequate extent with a still tolerable keyhole effect. A minimal distance however is advantageous compared to a direct contact, since on entry into the light filter of an optically less dense medium, i.e. with a smaller refractive index such as air for instance, the light is greatly refracted towards the axis of incidence and on exit out of the light filter is correspondingly greatly refracted away from the axis of incidence, by which means the keyhole effect is reduced. Given a direct contact, specifically the refraction on entry into the light filter would be significantly lower towards the axis of incidence, by which means a share of the light beams which are irradiated obliquely from the second LED would possibly no longer be refracted towards the light irradiation side of the light filter, but would be lost in the cylinder lateral surface of the light filter.

Optionally, the light filter and the second LED can be arranged in a recess in a wall of the insertion section, wherein the wall defines an outer surface and the distance of a light irradiation side of the second LED to the outer surface at the most is two thirds of the diameter of the recess. The outer surface can preferably be a face surface of the insertion section. The recess, in which the second LED is seated, causes a certain "tunnel vision" or keyhole effect, since the second LED is arranged set back in the viewing direction with respect to the outer surface on account of the light filter which is arranged in front. Given a larger distance than two thirds of the diameter, the "tunnel vision" or the keyhole effect leads to too small a spatial angle being able to be adequately illuminated.

Optionally, the second light spectrum of the second LED and the transmission spectrum of the light filter in the second wavelength region between 550 nm and 700 nm can decrease with an increasing wavelength and the transmission of the light filter for light emitted by the second LED with a wavelength of 600 nm can be 20% to 45%. Herewith, the second LED and the light filter complement one another into sufficiently filtering out the second, red wavelength region given a thin as possible thickness of the light filter, in order to achieve a colour-true imaging for white light endoscopy without an additional corrective filter in the picture path in front of the picture sensor.

Optionally, at least one protective element which is transparent to white light can be arranged in front of the light irradiation side of the first LED and/or of a light outlet side of the light filter in the viewing direction, wherein the thickness of the protective element in the viewing direction is thinner than the thickness of the light filter in the viewing direction. The at least one protective element can herein be a thin as possible protective glass, protective plastic and/or a silicon dioxide layer which is deposited on the first LED or on the light filter. The protective element can protect the light filter and/or the first LED from mechanical damage such as scratches and chemical damage such as for instance due to aggressive body fluids, cleaning or processing media and/or oxidation.

Optionally, the at least one protective element is in direct contact with the light irradiation side of the first LED or with the light outlet side of the light filter or the distance of the at least one protective element to the light irradiation side of the first LED or to the light outlet side of the light filter is less than 10% of the thickness of the light filter in the viewing direction. This is advantageous, in order to be able to arrange the second LED as far as possible to the front in the viewing direction, in order to be able to adequately illuminate a large as possible spatial angle with a still tolerable keyhole effect.

Optionally, the light filter and/or the second LED can be surrounded by a mirroring cylinder lateral inner surface which extends essentially in the viewing direction. The cylinder lateral inner surface can be formed for example by a recess in the wall of the insertion section. Alternatively or additionally to this, the mirroring cylinder lateral inner surface can be deposited on a cylinder outer surface of the light filter and/or of the second LED as a radially inwardly mirroring layer.

Optionally, a plurality of n≥2 first LEDs and/or a plurality of m≥2 second LEDs can be arranged in the insertion section in a plane which is perpendicular to the viewing direction, n-times and m-times respectively in a rotationally symmetrical manner with respect to the viewing direction axis of the picture sensor. By way of this, an undesirable shadowing is reduced for the white light endoscopy as well as for fluorescence endoscopy. Herein, an equal number of first LEDs and second LEDs, thus n=m can be provided, these being arranged in a circle around the picture sensor such that first LEDs and second LEDs alternate in a circularly peripheral manner. If the second LEDs are used as relative light-weak blue LEDs for fluorescence endoscopy, it can however be advantageous for example to provide more second LEDs than first LEDs, thus m>n.

The disclosure is hereinafter explained in more detail by way of an embodiment example which is represented in the drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIGS. 6 and 7 are graphs showing light spectra of the first and second LED according to an embodiment example of the medical-endoscopic instrument which is disclosed herein.

DESCRIPTION OF PREFERRED EMBODIMENTS

Figure 1:
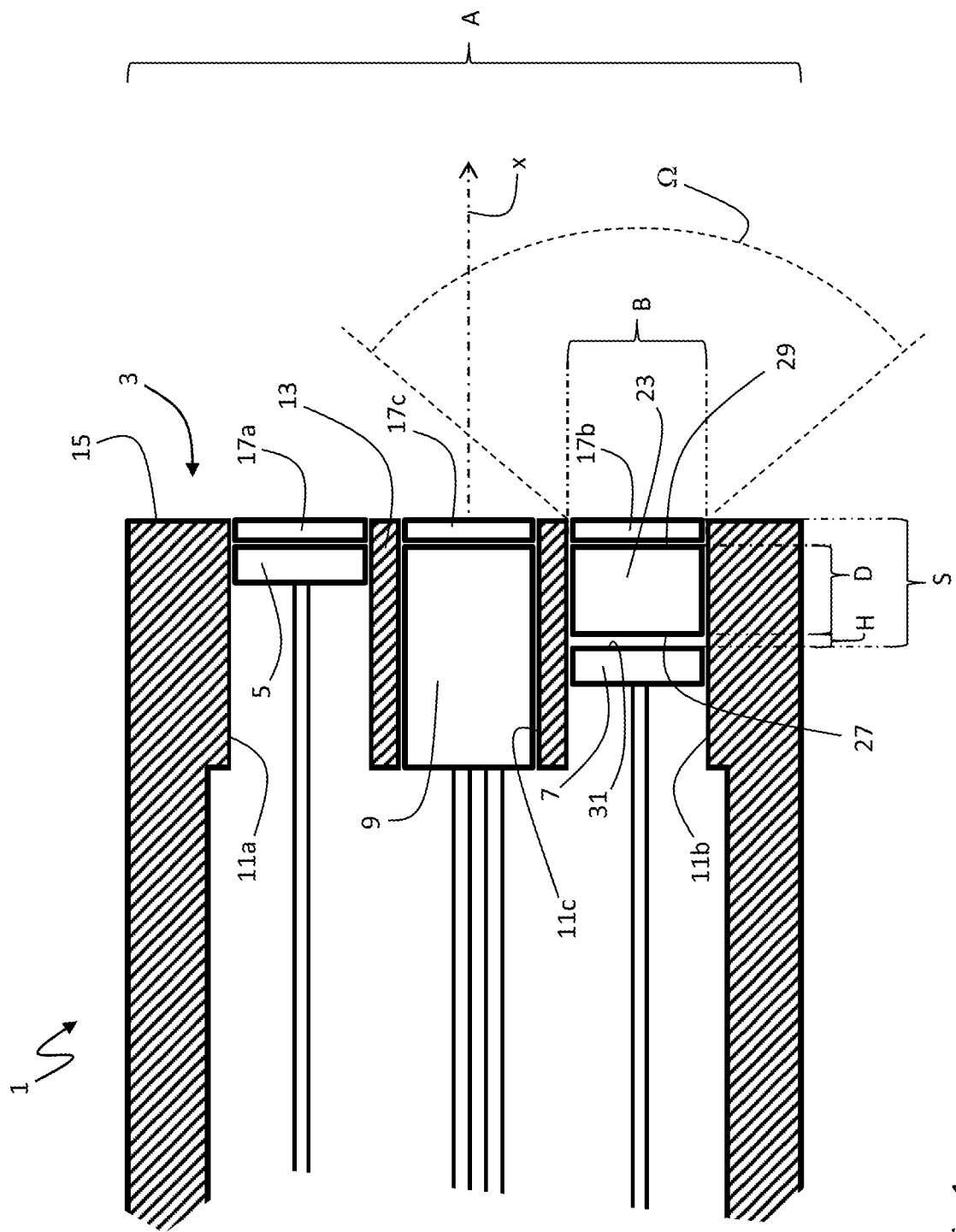
FIG. 1 is a schematic longitudinal sectional view through a distal section of an insertion section according to a first embodiment example of the medical-endoscopic instrument which is disclosed herein.

Referring to the drawings, FIG. 1 shows a distal end section of an insertion section 1 of a medical-endoscopic instrument. The insertion section 1 is provided for being introduced into a human or animal body in a minimal-invasive manner, in order to be able to illuminate or irradiate this with light and to permit a video or picture transmission from the inside of the body. In order to fashion the insertion in a minimal-invasive manner, an outer diameter A of the insertion section 1 is small as possible and in this embodiment example is less that 5 mm.

A first LED 5, a second LED 7 and a picture sensor 9 are arranged next to one another on a distal face side 3 of the insertion section 1 and are aligned in a common viewing direction x which in this embodiment example corresponds to the longitudinal direction of the insertion section 1. The first LED 5, the second LED 7 and the picture sensor 9 are each arranged in a recess 11a, b, c in a face wall 13 of the insertion section 1. The face wall 13 defines an outer surface 15 on the face side 3 of the insertion section 1. The first LED 5, the second LED 7 and the picture sensor 9 are each arranged behind the protective elements 17a, b, c in the form of thin protective glass discs which are all flush with the outer surface 15 on the face side 3 of the insertion section 1 and which protect from mechanical damage such as scratches and chemical damage such as for instance due to aggressive body fluids, cleaning or processing media and/or oxidation. The protective elements 17a, b, c can also be configured as a common protective glass disc which encompasses the first LED 5, the second LED 7 and the picture sensor 9. The protective elements 17a, b, c are transparent to white light and in this embodiment example have a refractive index of at least 1.75 as well as a greater tensile strength and hardness than conventional optical glass. The protective elements 17a, b, c can be configured from a synthetic, mono-crystalline crystal.

The first LED 5 has a first light spectrum 19 (see FIG. 6) which is suitable for fluorescence endoscopy and which here has a peak at 406 nm with a half-width of 12 nm in the blue wavelength region. A photo sensibiliser which selectively builds up on pathological tissue can be made to fluoresce in the red wavelength region with this blue light of the first LED 5 within the framework of a photodynamic diagnosis (PDD) and/or a photodynamic therapy (PDT). Such a fluorescing in the red wavelength region can be easily recorded by the pictures sensor 9, in front of which no corrective filter is arranged. An objective and/or a long-pass filter can be arranged in front of the picture sensor 9 (not shown in FIG. 1). However, such a long-pass filter does not represent a corrective filter for balancing the spectral sensor sensitivity to the spectral sensitivity of the human eye, but merely blocks short-waved blue light of the first LED 5 which is scattered back from the body in a direct manner.

The second LED 7 has a second light spectrum 21 (see FIG. 7) which is suitable for white light endoscopy and which here has a peak in a first wavelength region K of 400 nm to 500 nm and reduces with an increasing wavelength in a second wavelength region L of 550 nm to 700 nm. Alternatively to the first light spectrum 19 which is represented in FIG. 6, the first LED 5 can have the same light spectrum 21 as the second LED 7, inasmuch as the fluorescence excitation which is necessary for the envisaged fluorescence endoscopy can be effected herewith.

In this case, the first LED 5 and the second LED 7 can be of the same type.

The second LED 7 in this embodiment example is arranged offset to the rear relative to the first LED 5 with respect to the viewing direction x. This is due to the fact that an infrared blocking filter 23 which has a transmission spectrum 25 according to one of the FIG. 8 to 11 is arranged in front of the second LED 7 and behind the protective element 17b. The light of the second LED 7 which according to the second light spectrum 21 (see FIG. 7) on average irradiates significantly more intensely in the lower first wavelength region K than in the upper second wavelength region L, on average is let through by the infrared blocking filter 23, according to the transmission spectrum 25 (see FIGS. 8 and 11), less in the upper second wavelength region L than in the first wavelength region K. The second light spectrum 21 of the second LED 7 and the transmission spectrum 25 of the infrared blocking filter 23 therefore complement one another on reducing the light in the upper second wavelength region L. This has the positive effect of the thickness D of the infrared blocking filter 23 between a light inlet side 27 of the infrared blocking filter 23 and a light outlet side 29 of the infrared blocking filter 23 being able to be configured more thinly, so that the distance S from the light outlet side 29 of the second LED 7 to the outer surface 15, by which the second LED 7 must be displaced (offset) to the rear due to the infrared blocking filter 23, turns out as low as possible.

The recess 11b in a face wall 13 of the insertion section 1, in which recess the second LED 7, the infrared blocking filter 23 and the protective element 17b are recessed in an exactly fitting manner, here has a diameter B. The recess 11b can be provided with a mirroring cylinder lateral inner surface, but this is not a necessity, since the keyhole effect can already be reduced to a sufficient extent by way of other measures in the embodiments which are described here. Alternatively to the face wall 13, a sleeve with an inner diameter B could also encompass the second LED 7, the infrared blocking filter 23 and the protective element 17b in an exactly fitting manner and additionally in a possibly mirroring manner. The radial outer surface of the infrared blocking filter 23 could possibly be provided with a mirroring metal layer.

The ratio B/S of the diameter B and the distance S between the light outlet side 29 and the second LED 7 and the outer surface 15, by which the second LED 7 is displaced or offset to the rear due to the infrared blocking filter 23 determines a spatial angle Ω which is illuminated by the second LED 7. The illuminated spatial angle Ω should be at least 2.24 steradians, i.e. about 35% of a unit hemisphere, in order to reduce a keyhole effect where possible. The ratio B/S here is about 1.5.

In order to keep the distance S as short as possible, thus on the one hand a small as possible thickness D of the infrared blocking filter 23 is selected, e.g. 0.3 mm to 80% of the diameter B, this still providing an adequately high filtering effect. On the other hand, a minimal distance H of less that 10% of the thickness D of the infrared blocking filter 23 lies between a light irradiation side 31 of the second LED 7 and the light inlet side 27 of the infrared blocking filter 23, in order utilise a refraction towards the axis of incidence on entry into the infrared blocking filter 23, so as to reduce the keyhole effect.

Figure 3:
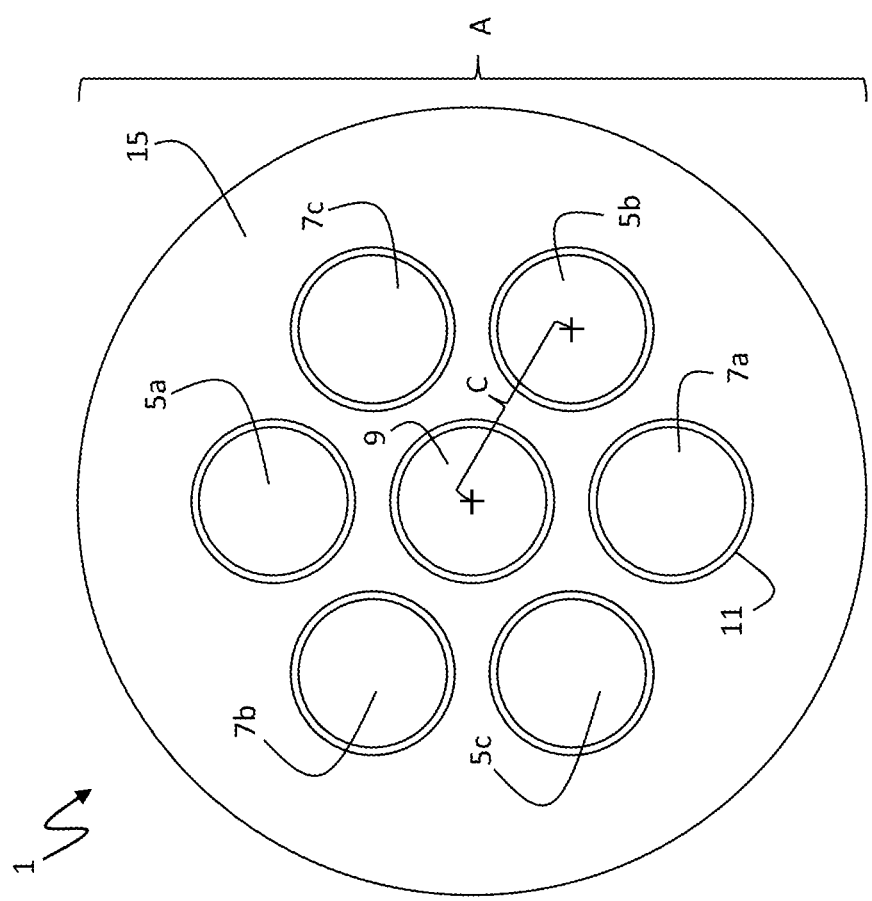
FIGS. 2 and 3 are front views upon a face side of the insertion section according to two embodiment examples of the medical endoscopic instrument, which is disclosed herein.
Figure 2:
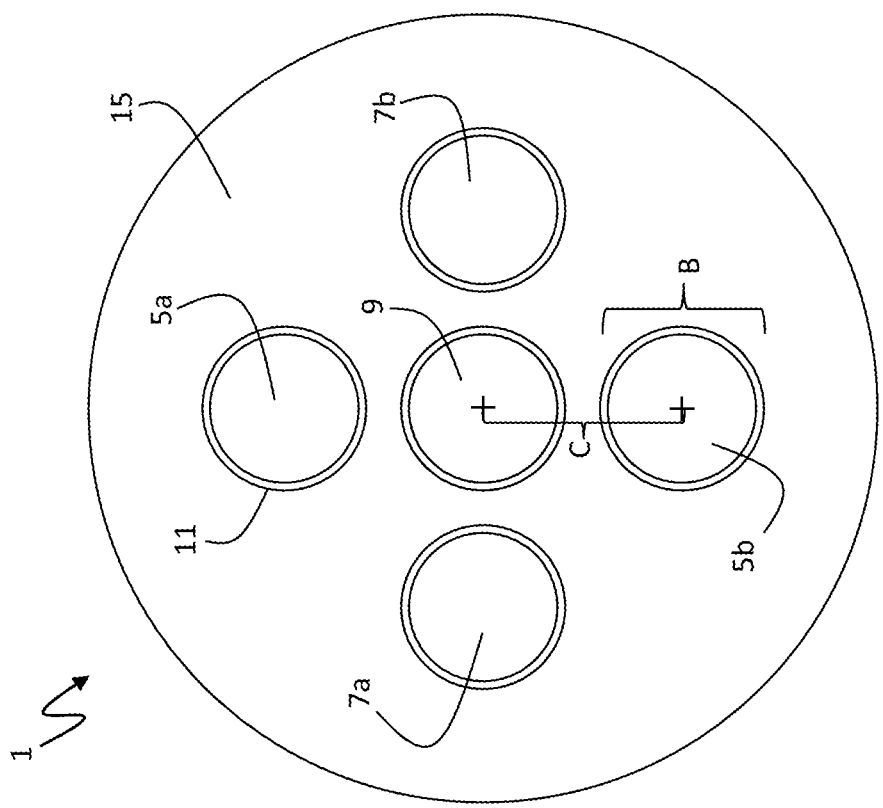
Figure 5:
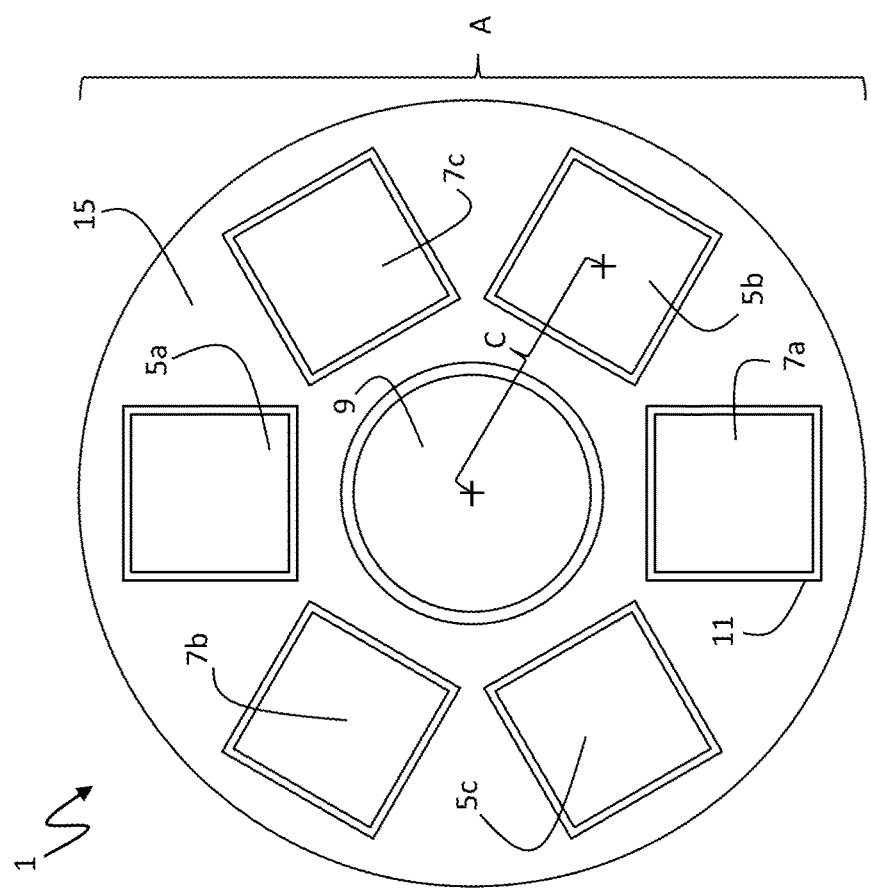
FIGS. 4 and 5 are front views upon a face side of an insertion section according to two further embodiment examples of the medical-endoscopic instrument which is disclosed herein.
Figure 4:
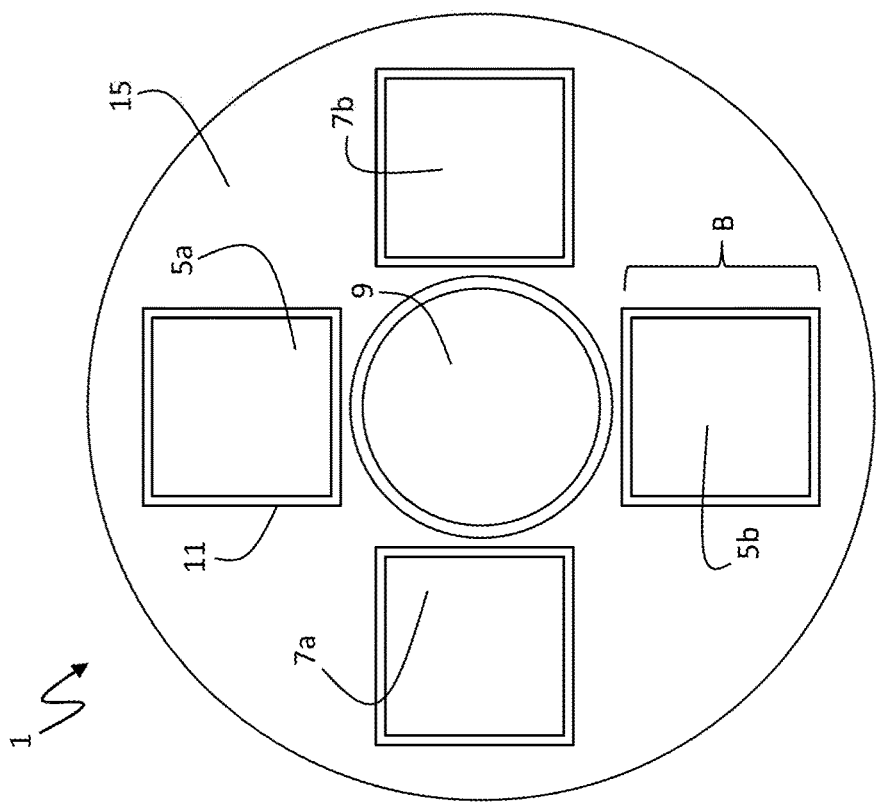

Different embodiment examples with a plurality of first LEDs 5a-c and second LEDs 7a-c are shown in the front views onto the face side 3 of the insertion section 1 according to the FIGS. 2 to 5. The picture sensor 9 is arranged coaxially centrally in the face wall 13 of the insertion section 1. A plurality of n≥2 first LEDs 5a-c and a plurality of m≥2 second LEDs are arranged in the insertion section 1 around the picture sensor 9 in a plane perpendicular to the viewing direction x, n-times or m-times in a rotationally symmetrical manner with respect to the viewing direction axis x of the picture sensor. In FIGS. 2 and 4 n=2 and m=2, wherein the first LEDs 5a, b each lying diametrically opposite one another have the same distance C to the central picture sensor 9 as the second LEDs 7a, b which each likewise lie diametrically opposite one another. In FIGS. 3 and 5, n=3 and m=3, wherein the first LEDs 5a-c each arranged lying circumferentially offset to one another by 120° have the same distance C to the central picture sensor 9 as the second LEDs 7a, b which likewise each lie circumferentially offset to one another by 120°. In the embodiment examples of FIGS. 4 and 5, the recesses 11 in contrast to the embodiment examples of the FIGS. 2 and 3 do not have a circular cross section, but a rectangular or square cross section. In the case of a rectangular recess 11, the diameter B corresponds to the length of the shorter rectangle side.

The first light spectrum 19 of the first LED 5 and the second light spectrum of the second LED 7 are shown by way of example in FIGS. 6 and 7, wherein alternatively the first light spectrum 19 of the first LED 5 can be the same as the second light spectrum 21 of the second LED 7. The first LEDS 5 here is a blue LED with the first light spectrum 19 which is suitable for fluorescence endoscopy and has a peak at 406 nm with a half-width of 12 nm in the blue wavelength region. The second LED 5 here is a white-illuminating LED with the second light spectrum 21 which here has a peak in the first wavelength region K of 400 nm to 550 nm and reduces with an increasing wavelength in the second wavelength region L of 550 to 700 nm. On average, the second LED 5 therefore illuminates more intensely in the first wavelength region than in the second wavelength region L. In the FIGS. 5 and 7, a relative intensity Ira is plotted over the wavelength λ in nm in a dimensionless manner. The relative intensity $I_{rel}$ is defined such that it is 1 at an intensity maximum. The average intensity in a wavelength region between a wavelength $\lambda_1$ and a wavelength $\lambda_2$ is defined here as $$\overline{I} = \int_{\lambda_1}^{\lambda_2} \frac{I(\lambda)}{\lambda_2 - \lambda_1} d\lambda.$$

If therefore the first wavelength region K extends from a wavelength $\lambda_1$=400 to a wavelength $\lambda_2$=550, and the second wavelength region L extends from a wavelength $\lambda_3$=550 nm to a wavelength $\lambda_4$=700 nm, then here $$\overline{I_1} = \int_{\lambda_1}^{\lambda_2} \frac{I_1(\lambda)}{\lambda_2 - \lambda_1} d\lambda = 0.5 > \overline{I_2} = \int_{\lambda_3}^{\lambda_4} \frac{I_2(\lambda)}{\lambda_4 - \lambda_3} d\lambda = 0.3.$$

Figure 8:
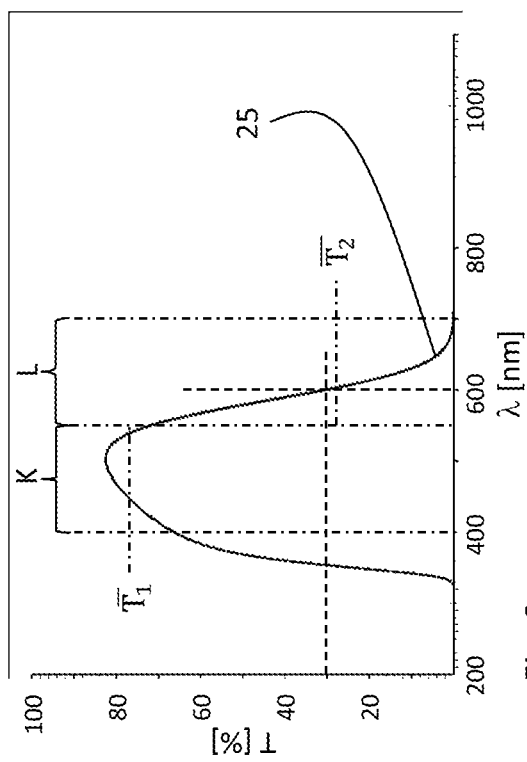
FIGS. 8 to 11 are graphs showing different exemplary transmission spectra of the light filter according to embodiment examples of the medical-endoscopic instrument which is disclosed herein.
Figure 9:
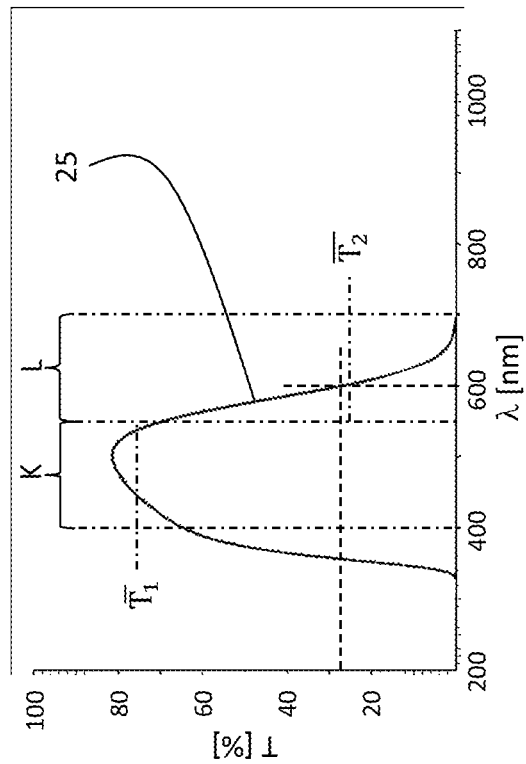
Figure 10:
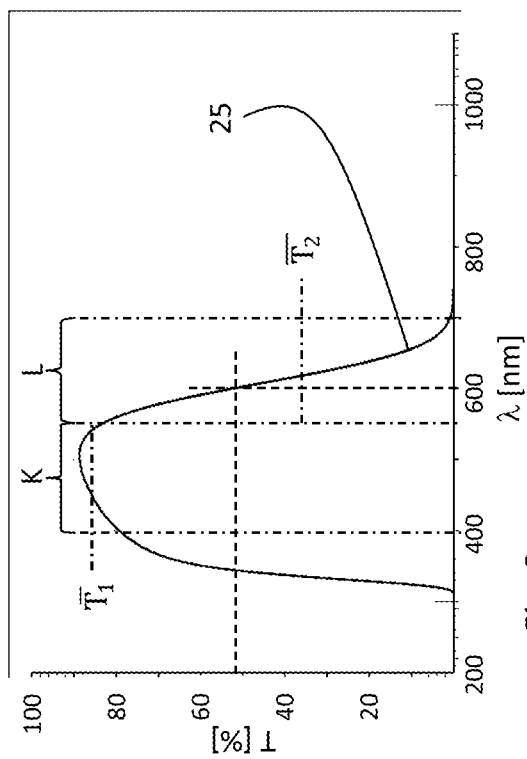
Figure 11:
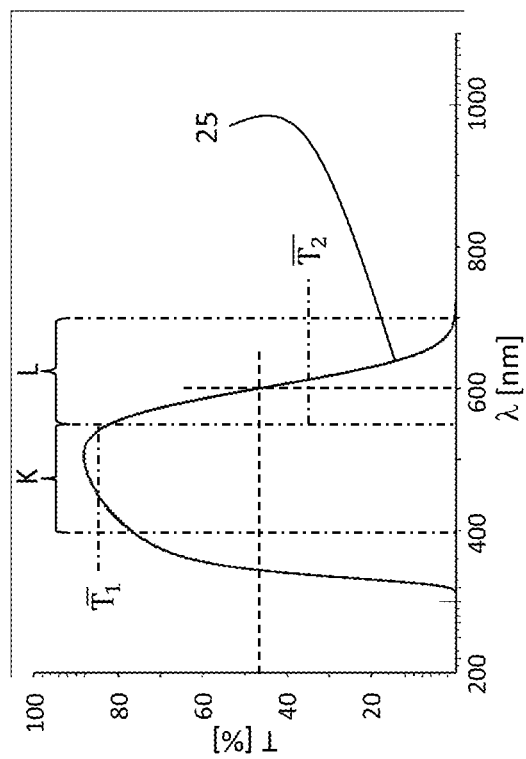

The transmission spectra 25 of the infrared blocking filter 23 which are shown in FIGS. 8 to 11 by way of example correspond to different filter types and filter thicknesses. In FIG. 8, the transmission spectrum 25 of a band filter BG 39 (blue glass) of the company Schott with a thickness of 1 mm is shown. The same infrared blocking filter 23 with a thickness of 1.2 mm is shown in FIG. 10. One recognises that the transmission spectrum 25 is scaled with the thickness D of the infrared blocking filter 23. For example, the transmission at 600 nm is about 51% at 1 mm thickness and is then only 46% at 1.2 mm thickness. A greater filter effect in the upper wavelength region L can then be achieved by a different filter glass. The transmission spectrum 25 of a band filter BG (blue glass) of the company Schott with a thickness of 1 mm is shown in FIG. 9. Here, the transmission at 600 nm is only about 28% given 1 mm thickness. The band filter BG 67 (blue glass) of the company Schott, whose transmission spectrum 25 is shown in FIG. 11 for a thickness of 0.67 mm can also be used in order to further reduce the thickness D. The transmission at 600 nm here likewise lies below 30%.

One can switch between fluorescence endoscopy and white light endoscopy in a simple and rapid manner with only the one picture sensor 9 due to the possibility of fluorescence light with the first LED 5 and by way of white light with the second LED 7, filtered by way of the light filter 23. The picture sensor 9 herein makes do without a corrective filter in the form of a short-pass filter and on account of this is more efficient, particularly with white-light endoscopy, since long-waved light which heats tissue and for which the picture sensor 9 is too sensitive in any case for white light endoscopy, by way of the combination of the light of the second LED 7 which is already weaker in the upper wavelength region and the infrared blocking filter 23, is not irradiated by the instrument in the first place. A keyhole effect can be reduced by way of suitable selection of the infrared blocking filter 23 with a suitable thickness given the diameter B which is restricted for minimal-invasive operations.

The numbered designations of the components or movement directions as "first", "second", "third" etc. have herein only been selected purely randomly, so as to differentiate the components or movement directions from one another, and can be selected arbitrarily differently. They therefore do not imply any status of significance. A designation of a component or technical feature as "first" should not be misunderstood to the extent that there must be a second component or technical feature of this type. Moreover, any method steps, inasmuch as not explicitly stated otherwise or not compelling necessary, can be carried out in an arbitrary sequence and/or in a party or completely overlapping manner with regard to time.

Equivalent embodiments of the parameters, components or functions which are described herein and which, in the light of this description, appear to be evident to the person whose is competently skilled are included herein as if they were explicitly described. Accordingly, the protective scope of the claims is to include such equivalent embodiments. "Can" features which are indicated as optional, advantageous, preferred, desired or similar are to be understood as being optional and not as limiting the protective scope.

The described embodiments are to be understood as illustrative examples and do not represent a final list of possible embodiments. Each feature which has been disclosed in the framework of an embodiment can be used alone or in combination with one or more other features, independently of the embodiment, in which the features have been described in each case. Whereas at least one embodiment is described and shown herein, modifications and alternative embodiments which appear to be evident to a competently skilled person in the light of this description are also included by the protective scope of this disclosure. Moreover, the term "comprise" is neither to exclude additional other features or method steps nor does the term "one" exclude a plurality.

While specific embodiments of the invention have been shown and described in detail to illustrate the application of the principles of the invention, it will be understood that the invention may be embodied otherwise without departing from such principles.

The invention claimed is:

1. A medical-endoscopic instrument with a distal elongate insertion section for the minimal-invasive introduction into a human or animal body, wherein the insertion section comprises:

at least one first LED;
a second LED;
a picture sensor, wherein the first LED, the second LED and the picture sensor are aligned in a common viewing direction, the first LED comprises a first light spectrum which is suitable for fluorescence endoscopy and the second LED comprises a second light spectrum which is suitable for white light endoscopy; and
a light filter arranged in front of the second LED in the viewing direction, wherein the light filter has a transmission spectrum, wherein the second LED is configured to irradiate according to the second light spectrum on average more intensively in a first wavelength region than in a second wavelength region, and wherein the light filter is configured to let through light which is emitted by the second LED, according to the transmission spectrum, on average less in the second wavelength region than in the first wavelength region.

2. A medical-endoscopic instrument according to claim 1, wherein the first LED, the second LED and the picture sensor are arranged on a common wall of the insertion section.

3. A medical-endoscopic instrument according to claim 1, wherein the first LED, the second LED and the picture sensor are arranged on a distal face side of the insertion section and the viewing direction runs distally in a longitudinal direction of the insertion section.

4. A medical-endoscopic instrument according to claim 1, wherein the first LED is arranged offset to the front relative to the second LED with respect to the viewing direction.

5. A medical-endoscopic instrument according to claim 1, wherein the light filter is an absorption filter.

6. A medical-endoscopic instrument according to claim 1, wherein the light filter is an infrared blocking filter, wherein the first wavelength region lies in the visible light spectrum below 550 nm and the second wavelength region in the visible light spectrum above 550 nm.

7. A medical-endoscopic instrument according to claim 1, wherein the picture sensor in a plane which is perpendicular to the viewing direction has a same distance to the first LED as to the second LED.

8. A medical-endoscopic instrument according to claim 1, wherein the first light spectrum and the second light spectrum are different or identical.

9. A medical-endoscopic instrument according to claim 1, wherein the first LED is an LED which emits white light and the second LED is an LED which emits blue light, or the first LED and the second LED are of the same type.

10. A medical-endoscopic instrument according to claim 1, wherein the light filter comprises a light inlet side and a light outlet side and between the light inlet side and light outlet side in the viewing direction the light filter has a thickness and orthogonally to the viewing direction a diameter, wherein the thickness is 0.3 mm up to 80% of the diameter.

11. A medical-endoscopic instrument according to claim 1, wherein the light filter has a light inlet side and a light outlet side and a thickness of 0.3 mm to 1.2 mm between the light inlet side and the light outlet side in the viewing direction.

12. A medical-endoscopic instrument according to claim 11, wherein the distance of the light inlet side of the light filter to the light irradiation side of the second LED is less than 30% of the thickness of the light filter in the viewing direction.

13. A medical-endoscopic instrument according to claim 1, wherein the light filter and the second LED are arranged in a recess in a wall of the insertion section, wherein the wall defines an outer surface and a distance of a light irradiation side of the second LED to the outer surface at the most is two thirds of a diameter of the recess.

14. A medical-endoscopic instrument according to claim 1, wherein the second light spectrum of the second LED and the transmission spectrum of the light filter in the second wavelength region between 550 nm and 700 nm decreases with an increasing wavelength and the transmission of the light filter for light emitted by the second LED with a wavelength of 600 nm is 20% to 45%.

15. A medical-endoscopic instrument according to claim 1, further comprising at least one protective element, which is transparent to white light, arranged in front of a light irradiation side of the first LED and/or of a light outlet side of the light filter in the viewing direction, wherein a thickness of the protective element in the viewing direction is thinner than a thickness of the light filter in the viewing direction.

16. A medical-endoscopic instrument according to claim 15, wherein the at least one protective element is in direct contact with the light irradiation side of the first LED or with the light outlet side of the light filter or a distance of the at least one protective element to the light irradiation side of the first LED or to the light outlet side of the light filter is less than 30% of the thickness of the light filter in the viewing direction.

17. A medical-endoscopic instrument according to claim 16, wherein the at least one protective element is a protective glass, a protective plastic and/or a silicon dioxide layer which is deposited on the first LED or on the light filter.

18. A medical-endoscopic instrument according to claim 1, wherein the light filter and/or the second LED are surrounded by a mirroring cylinder lateral inner surface which extends in the viewing direction.

19. A medical-endoscopic instrument according to claim 18, wherein the mirroring cylindrical lateral inner surface is formed by a recess in a wall of the insertion section.

20. A medical-endoscopic instrument according to claim 1, wherein a plurality of $n \geq 2$ first LEDs and/or a plurality of $m \geq 2$ second LEDs are arranged in the insertion section in a plane which is perpendicular to the viewing direction, n-times and m-times respectively in a rotationally symmetrical manner with respect to a viewing direction axis of the picture sensor, wherein n is a number of first LEDS and m is a number of second LEDS.

* * * * *